United States Patent
Fogal et al.

(10) Patent No.: US 11,434,197 B2
(45) Date of Patent: Sep. 6, 2022

(54) ENZYMATIC PROCESS FOR THE PREPARATION OF DROXIDOPA

(71) Applicant: F.I.S.—FABBRICA ITALIANA SINTETICI S.P.A., Montecchio Maggiore (IT)

(72) Inventors: Stefano Fogal, Montecchio Maggiore (IT); Paolo Stabile, Montecchio Maggiore (IT); Pierluigi Padovan, Montecchio Maggiore (IT); Matteo De Poli, Montecchio Maggiore (IT); Angelo Restelli, Montecchio Maggiore (IT)

(73) Assignee: F.I.S.—FABBRICA ITALIANA SINTETICI S.P.A., Montecchio Maggiore (IT)

( * ) Notice: Subject to any disclaimer, the term of this patent is extended or adjusted under 35 U.S.C. 154(b) by 87 days.

(21) Appl. No.: 17/059,594

(22) PCT Filed: Jun. 7, 2019

(86) PCT No.: PCT/EP2019/064979
§ 371 (c)(1),
(2) Date: Nov. 30, 2020

(87) PCT Pub. No.: WO2019/243087
PCT Pub. Date: Dec. 26, 2019

(65) Prior Publication Data
US 2021/0163401 A1 Jun. 3, 2021

(30) Foreign Application Priority Data
Jun. 21, 2018 (EP) .................................... 18179043

(51) Int. Cl.
| | | |
|---|---|---|
| C07C 227/20 | (2006.01) | |
| C12N 9/04 | (2006.01) | |
| C07C 227/18 | (2006.01) | |
| C07C 271/22 | (2006.01) | |
| C07C 269/06 | (2006.01) | |
| C12P 13/04 | (2006.01) | |
| C07C 229/36 | (2006.01) | |

(52) U.S. Cl.
CPC .......... C07C 227/20 (2013.01); C07C 227/18 (2013.01); C07C 269/06 (2013.01); C07C 271/22 (2013.01); C12N 9/0006 (2013.01); C12P 13/04 (2013.01); C12Y 101/01002 (2013.01); C07C 229/36 (2013.01); C12Y 101/01 (2013.01)

(58) Field of Classification Search
None
See application file for complete search history.

(56) References Cited

U.S. PATENT DOCUMENTS

| | | |
|---|---|---|
| 3,920,728 A | 11/1975 | Hegedus |
| 4,319,040 A | 3/1982 | Ohashi et al. |
| 4,480,109 A | 10/1984 | Ohashi et al. |
| 4,562,263 A | 12/1985 | Ohashi et al. |
| 2015/0344439 A1* | 12/2015 | De Lucchi ........... C07D 209/12 546/14 |
| 2017/0335357 A1 | 11/2017 | Divi et al. |

FOREIGN PATENT DOCUMENTS

| | | | | |
|---|---|---|---|---|
| EP | 0112606 A1 | | 7/1984 | |
| EP | 0375554 A2 | | 6/1990 | |
| JP | H02172956 | * | 7/1990 | ........... C07C 229/36 |
| JP | 2007190009 A | | 8/2007 | |

OTHER PUBLICATIONS

International Search Report and Written Opinion for Corresponding International Application No. PCT/EP2019/064979 (9 Pages) (Jul. 11, 2019).

* cited by examiner

*Primary Examiner* — Amy C Bonaparte
(74) *Attorney, Agent, or Firm* — Lucas & Mercanti, LLP

(57) ABSTRACT

The present invention relates to a process for the preparation of Droxidopa by means of an improved enzymatic reduction of a compound of formula (II): (II), wherein $R^1$, $R^2$ is independent hydrogen, acetyl, $R^3$ is hydrogen, a C1-C4 linear or branched alkyl group and $R^4$ is hydrogen or an amine protecting group.

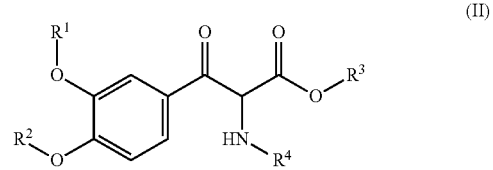

(II)

9 Claims, No Drawings

ENZYMATIC PROCESS FOR THE PREPARATION OF DROXIDOPA

CROSS-REFERENCE TO RELATED APPLICATIONS

This application is a 371 of PCT/EP2019/064979, filed Jun. 7, 2019, which claims the benefit of European Patent Application No. 18179043.7, filed Jun. 21, 2018.

TECHNICAL FIELD

The present invention relates to a process for the preparation of Droxidopa by means of enzymatic reduction.

BACKGROUND ART

Droxidopa is chemically known as (2S,3R)-2-amino-3-(3,4-dihydroxyphenyl)-3-hydroxypropanoie acid and it is structurally represented by the following formula (I). It is also known as L-threo-dihydroxyphenylserine, L-threo-DOPS, L-DOPS. Droxidopa is available in the market as Northera® as capsules with dosages of 100 mg, 200 mg and 300 mg for oral administration.

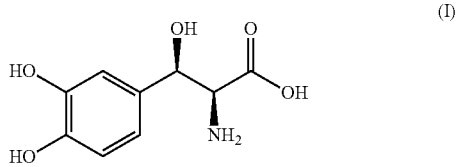

(I)

Droxidopa is an orally active, synthetic norepinephrine precursor that was originally launched in 1989 in Japan for the oral treatment of frozen gait or dizziness associated with Parkinson's disease and for the treatment of orthostatic hypotension, syncope or dizziness associated with Shy-Drager syndrome and familial amyloidotic polyneuropathy.

In 2011, the product was filed for approval in the U.S.A. and in 2014 Northera® was approved for the treatment of orthostatic dizziness, light headedness, or the "feeling that you are about to black out" in adult patients with symptomatic neurogenic orthostatic hypotension caused by primary autonomic failure, dopamine beta-hydroxylase deficiency, and non-diabetic autonomic neuropathy.

Droxidopa replenishes depleted norepinephrine, allowing for reuptake of norepinephrine into peripheral nervous system neurons. This reuptake, in turn, stimulates receptors far vasoconstriction, providing physiological improvement in symptomatic neurogenic orthostatic hypotension patients.

It has also shown efficacy in other diseases, such as depression.

Droxidopa is a synthetic amino acid analog that is directly metabolized to norepinephrine by dopadecarboxylase, which is extensively distributed throughout the body.

Its chemical preparation generally involves a multi-step synthesis.

Droxidopa is disclosed in U.S. Pat. No. 3,920,728 (hereinafter referred to as US'728 patent). The US'728 patent also provides a process for the preparation of droxidopa comprising the steps of (i) reaction of 3,4-dibenzyloxybenzaldehyde with glycine, followed by treatment with sodium acetate trihydrate and diethylamine to obtain racemic-threo/erythro-3-(3,4-dibenzyloxyphenyl)-serine; (ii) treatment of the compound obtained in step (i) with carbobenzoxy chloride to obtain racemic-threo/erythro-3-(3,4-dibenzyloxyphenyl)-N-carbobenzoxyserine; (iii) treatment of the compound obtained in step (ii) with dicyclohexylamine to obtain racemic-threo-3-(3,4-dibenzyloxyphenyl)-N-carbobenzoxyserine dicyclohexylamine salt, which by treatment with HCl gas in the presence of ethyl acetate yields racemic-threo-3-(3,4-dibenzyloxyphenyl)-N-carbobenzoxyserine; (iv) treatment of the compound obtained in step (iii) with (+)-ephedrine to yield (+)-ephedrine salt of L-threo-3-(3,4-dibenzyloxyphenyl)-N-carbobenzoxyserine; (v) hydrolysis of the compound obtained in step (iv) to yield L-threo-3-(3,4-dibenzyloxyphenyl)-N-carbobenzoxyserine and (vi) reduction of the compound obtained in step (v) over Pd/C to yield L-threo-3-(3,4-dibenzyloxyphenyl)-serine. The process disclosed in US'728 patent is an elaborate and tedious process for commercial manufacturing. Also, the chiral resolution to obtain threo/erythro isomer results into 50% loss of the undesired isomer, which affects the overall yield of the process.

Typically, one or more of the necessary steps in the synthesis require that reactive sites, other than the site targeted for the reaction, are temporarily protected.

Thus, the synthesis of Droxidopa typically comprises at least one protecting and associated deprotecting step. For example, the catechol moiety, the amine moiety, and/or the carboxyl moiety may require protection and subsequent deprotection, depending upon the synthetic route and the reagents used in the preparation of Droxidopa.

Several synthetic and enzymatic approaches to Droxidopa have been described in the literature.

Most of them entail the coupling between a conveniently protected 3,4-dihydroxy benzaldehyde with glycine to yield a diastereomerically enriched mixture of threo-DOPS.

This approach has been described in patent application JP 2007190009(A) and entails the coupling of glycine or a salt thereof with 3,4-dihydroxybenzaldehyde in the presence of a threonine aldolase to form the corresponding enantiomerically enriched amino acid derivative.

An alternative has been described in patent application EP0112606 A1, is not stereoselective and relies on fractional crystallizations to separate a threo/erythro mixture.

The diastereomerically enriched mixture of the protected threo-DOPS can be converted into the optically active D- and L-threo-DOPS by optically resolving a racemic mixture of threo-2-(3,4-methylenedioxyphenyl)-N-carbobenzyloxyserine or threo-2-(3,4-dibenzyloxy-phenyl)-N-carbobenzyloxyserine, as detailed in U.S. Pat. Nos. 4,319,040 and 4,480,109, respectively. Following optical resolution of these racemic mixtures to give the desired L-enantiomer, the methylenedioxy or benzyl groups must be removed from the catechol moiety and the carbobenzyloxy (Cbz) group must be removed from the amine group to give Droxidopa.

The U.S. Pat. No. 4,562,263 discloses a process for preparation of droxidopa comprising optical resolution of N-phthaloyl-3-(3,4-methylenedioxyphenyl)serine using optically active amine selected from the group consisting of strychinine, cinconidine, L-norephedrine, S-2-amino-1,1-diphenyl-1-propanol and L-3-hydroxy-3-(4-nitrophenyl)-2-amino-I-propanol to yield L-N-phthaloyl-3-(3,4-methylenedioxyphenyl)serine, reacting the resulting compound with a Lewis acid to form N-phthaloyl-3-(3,4-dihydroxyphenyl)-serine; which is then deprotected by removal of phthaloyl group with hydrazine to yield L-threo-3-(3,4-dihydroxyphenyl)-serine. The process involves use of complex agents for isomer separation, which also results in <50% of desired isomer. Also, the hydrazine used for the deprotection of phthaloyl group is known to be genotoxic and thus it is required to remove traces of hydrazine from the final product.

According to an alternative approach described in patent application EP 201039 A1, a racemic mixture of threo-2-(3,4-dibenzyloxy-phenyl)-N-acetylserine can be converted into L-threo-2-(3,4-dibenzyloxy-phenyl)-serine by treatment with a L-amino acylase.

A disadvantage associated with all the synthetic pathways cited above is that in converting a racemic starting material using an enantioselective enzyme or an optically active amine, a maximum yield of 50% of the enantiomerically pure end product can be reached.

The use of resolving agent renders the process costly. Partial recycling of the resolving agent is feasible but such recycling is costly as it requires additional processing and is also associated with waste generation. The undesired enantiomer cannot be recycled and is discarded.

This yield may be further reduced due to the need for high chiral purity (>95% enantiomeric excess).

An alternative procedure for the stereoselective preparation of Droxidopa has been described in patent application EP375554 A1. According to the latter, the two stereocenters are introduced simultaneously with a Noyori-type asymmetric hydrogenation with dynamic kinetic resolution (AH-DKR).

The process is particularly interesting because it is catalyzed by the cheapest of the transition metals (ruthenium) and of the chiral phosphines (Binap) employed in asymmetric hydrogenations.

However the proposed conditions are not conveniently suitable for an industrial production of Droxidopa, because: 100 bar of hydrogen pressure is out of range in normal industrial vessels; the reported reaction time is unpractical (almost 1 week); the best solvent is dichlorometane (which should be avoided for environmental concerns); and the deprotection of the methylenedioxy moiety requires large excesses of $AlCl_3$ or $AlBr_3$.

The said prior art processes are therefore disadvantageous for commercial manufacturing due to non-feasibility of the reaction process owing to use of genotoxic reagents, and due to the elaborate and tedious nature of the process, providing low yield of the desired isomer.

Thus, there is a clear need to develop an better route of synthesis which would provide the desired L-threo isomer in an efficient and more specific manner.

Thus, there is a need to develop a process for preparation of droxidopa, which avoids the synthetic process involving chiral resolution to obtain desired L-threo isomer, thereby making the process of the present invention simple, efficient, cost-effective and industrially feasible process.

SUMMARY OF INVENTION

The problem addressed by the present invention is therefore that of providing an better process for the preparation of the L-threo isomer of Droxidopa, the compound represented by formula (I), through an enantioselective process.

This problem is solved by a process for the preparation of Droxidopa as outlined in the annexed claims, whose definitions are integral part of the present description.

Particularly, the present invention provides a process for producing the active ingredient Droxidopa by means of enzymatic reduction of compound of formula (II):

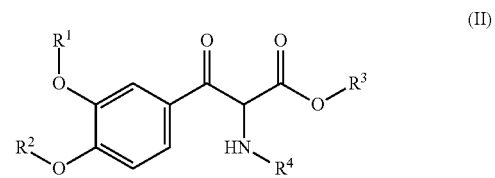

wherein $R^1$, $R^2$ is independently hydrogen, acetyl, $R^3$ is hydrogen, a $C_1$-$C_4$ linear or branched alkyl group and $R^4$ is hydrogen or an amine protecting group.

Preferably, said enzymatic reduction is carried out by the ketoreductase enzyme named KRED® 130.

In a further aspect, the present invention provides the use of a ketoreductase for the enzymatic reduction of compound of formula (II).

Aim of this invention is to provide a chemoenzymatic method to prepare Droxidopa or intermediates useful in the synthesis thereof, characterized by high yields and levels of stereocontrol avoiding the use of dangerous reagents and providing the desired compounds with an appropriate purity for the use in pharmaceuticals.

DESCRIPTION OF EMBODIMENTS

The object of present invention is a process for the preparation of Droxidopa of formula (I) or salt thereof:

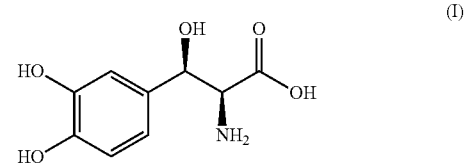 [SMILES: N[C@H](C(=O)O)[C@H](O)c1ccc(O)c(O)c1]

comprising the following steps:
A) enzymatic reduction of a compound of formula (II):

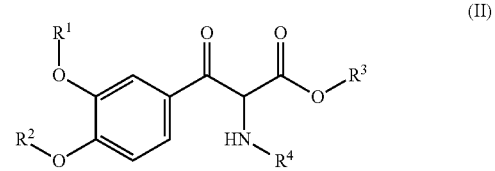

wherein $R^1$, $R^2$ are independently hydrogen or acetyl, $R^3$ is hydrogen or a $C_1$-$C_4$ linear or branched alkyl group and $R^4$ is hydrogen or an amine protecting group;
to give the compound of formula (III):

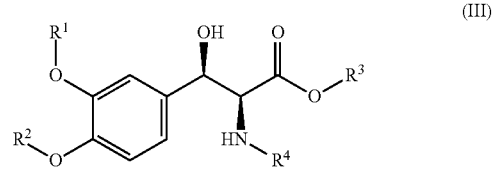

wherein $R^1$, $R^2$, $R^3$, $R^4$ have the same meaning of above; by means of a ketoreductase enzyme;
B) conversion of the compound of formula (III) obtained in the step a) to Droxidopa of formula (I).

According to the invention, the process provide the L-threo-3,4-Dihydroxyphenylserine of formula (I):

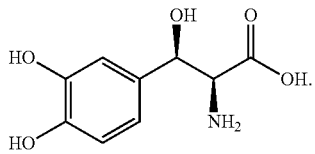

(I)

The compound of formula (I) having the configuration, on the two stereogenic carbons, i.e. C bonded to hydroxyl group and C bonded to amino group, respectively R and S. Accordingly to the name (2S,3R)-3-(3,4-Dihydroxyphenyl)-2-amino-3-hydroxypropanoic acid.

In an alternative embodiments in the compounds of formula (II) and (III), $R^1$ and $R^2$ could be independently methyl, benzyl, or a $C_1$-$C_4$ alkyl groups jointed to form a cycle.

According the preferred embodiment, in the compounds of formula (II) and (III) the $R^3$ is ethyl or methyl. More preferred $R^3$ is ethyl.

The definition of linear or branched $C_1$-$C_4$ alkyl thus also includes methyl, ethyl, n-propyl, isopropyl, n-butyl, isobutyl, sec-butyl, tert-butyl.

$R^4$ could be hydrogen or an amine protecting group which can be selected in the group comprising benzyl, formyl, acetyl, benzoyl, phenylsulfonyl, tolylsulfonyl, methylsulfonyl, (CO)OR$^5$ or (CO)R$^5$ where $R^5$ is $C_1$-$C_5$ linear or branched alkyl or $R^5$ is aryl-$C_{0-4}$ alkyl or $C_{0-4}$ alkyl-(unsubstituted or substituted aryl).

The linear or branched $C_{1-5}$ alkyl group of $R^5$ can also be, unsubstituted or substituted with one, two or three substituents chosen in the group of hydroxyl and $C_{1-5}$ alkoxy.

The definition of linear or branched $C_1$-$C_5$ alkyl thus also includes methyl, ethyl, n-propyl, isopropyl, n-butyl, isobutyl, sec-butyl, tert-butyl, n-pentyl, neopentyl, 1-methylbutyl, 2-methylbutyl, 3-methylbutyl, 1,1-dimethylpropyl, 1,2-dimethylpropyl, 2,2-dimethylpropyl, 1-ethylpropyl.

Preferred $R^4$ groups are pivaloyl, t-butyloxycabonyl (synonymous: tert-butyloxycarbonyl, Boc, terbutylcarbamate), methylcarbamate, ethylcarbamate or benzyloxycabonyl (Z or Cbz). More preferred $R^4$ groups are terbutylcarbamate, methylcarbamate, ethylcarbamate or benzyloxycabonyl (Z or Cbz).

According to the preferred embodiment, in the compounds of formula (II) and (III) the $R^3$ is ethyl and $R^4$ is terbutylcarbamate.

It has indeed surprisingly found that it is possible to carry out the enzymatic reduction of the keto group and the simultaneously generation a stereocenter on the side carbon, by an ketoreductase enzymes (abbreviated KRED).

The enzyme further to the enantioselective reduction, indeed, and surprisingly, induce the enantioselection on the adjacent carbon bonding the amino group.

In one embodiment. of the invention, the compound of formula (II) is preferably reduced to a compound of formula (III) using a chiral reducing agent, such as a reducing enzyme, preferably a ketoreductase (KRED) or a carbonyl reductase. Preferably, the chiral reducing agent is a KRED enzyme.

KRED enzymes belonging to class EC 1.1.1.184 are useful for the synthesis of optically active alcohols from the corresponding pro-stereoisomeric ketone substrates and by stereospecific reduction of corresponding racemic ketone substrates.

KRED enzymes typically convert a ketone substrate to the corresponding alcohol product, but may also catalyse the reverse reaction, oxidation of an alcohol substrate to the corresponding ketone product. The reduction of ketones and the oxidation of alcohols by enzymes such as KRED typically require a cofactor.

Typically, the reduction step is carried out by reacting compound of formula (II) with ketoreductase enzyme in the presence of cofactor for the ketoreduction and optionally a cofactor regenerating system.

Ketoreductase enzymes are commercially available, for example, from Codexis, Inc (USA).

The KRED can be found in a wide range of bacteria and yeast, for reviews: Kraus and Waldman, Enzyme' catalysis in organic synthesis, Vols. 1 and 2. VCH Weinheim 1995; Faber, K., Biotransformations in organic chemistry, 4th Ed. Springer, Berlin Heidelberg New York. 2000; Hummel and Kuia, 1989, Eur. J. Biochem. 184: 1-13. Several KRED gene and enzyme sequences have been reported, e.g., *Candida magnoliae* (Genbank Ace. No. JC7338; GL 1 1360538) *Candida parapsilosis* (Genbank Ace. No. BAA24528. I; GI:2815409), *Sporobolomyces salmonicolor* (Genbank Ace. No. AF160799; GL653973.

The KRED can be a wild type or a variant enzyme. Sequences of wild type and variant KRED enzymes are provided in WO2005/017135. KRED enzymes are commercially available, for instance supplied by Codexis. Examples of these include but are not limited to KRED-101, KRED-119, KRED-130, KRED-NADH-101, KRED.NAbff: 0.110, KRED-P1-A04, KRED-P1-B02, KRED-P1-BO5, KRED-P1-B05, KRED-P1-B10, KRED-P1-B12, KRED-P1-001, KRED-P1-H08, KRED-P1-H10, KRED-P2-B02, KRED-P2-C02, KRED-P2-C1 1, KRED-P2-D03, KRED-P2-D1 1, KRED-P2-D12, KRED-P2-G03, KRED-P2-H07, KRED-P3-B03, KRED-P3-G09, KRED-P3-H12 and combinations thereof. Most preferably the enzyme is KRED-130.

In the one preferred embodiment the KRED is KRED-130.

According to the preferred embodiment, the enzymatic reduction of the present invention can be carried out by the ketoreductase KRED® 130 and in the compound of formula (II) $R^3$ is ethyl and $R^4$ is terbutilcarbamate.

Preferably, the ketoreductase is isolated. The ketoreductase can be separated from any host, such as mammals, filamentous fungi, yeasts, and bacteria. The isolation, purification, and characterization of a NADH-dependent ketoreductase is described in, for example, in Kosjek et al., Purification and Characterization of a Chemotolerant Alcohol Dehydrogenase Applicable to Coupled Redox Reactions, Biotechnology and Bioengineering, 86:55-62 (2004).

Preferably, the ketoreductase is synthesized. The ketoreductase can be synthesized chemically or using recombinant means. The chemical and recombinant production of ketoreductases is described in, for example, in EP0918090(A2). Preferably, the ketoreductase is synthesized using recombinant means in *Escherichia coli*. Preferably, the ketoreductase is purified, preferably with a purity of about 90% or more, more preferably with a purity of about 95% or more. Preferably, the ketoreductase is substantially cell-free.

As used herein, the term "cofactor" refers to a non-protein compound that operates in combination with a ketoreductase enzyme. Cofactors suitable for use with ketoreductase enzymes include, but are not limited to nicotinamide adenine dinucleotide phosphate (NADP+), reduced nicotinamide adenine dinucleotide phosphate (NADPH), nicotinamide adenine dinucleotide (NAD+) and reduced nicotinamide adenine dinucleotide (NADH). Generally the reduced form of the cofactor is added to the reaction mixture.

KRED enzymes often can use either the phosphorylated or the non-phosphorylated cofactor.

KRED enzymes can be used in place of chemical procedures for the conversion of different keto compounds to chiral alcohol products. These biocatalytic conversions can employ whole cells expressing the ketoreductase for biocatalytic ketone reductions, or purified enzymes, particularly in those instances where presence of multiple ketoreductases in whole cells would adversely affect the enantiomeric purity and yield of the desired product. For in vitro applications, a cofactor (NADH or NADPH) regenerating enzyme such as glucose dehydrogenase (GDH) and formate dehydrogenase typically is used in conjunction with the ketoreductase.

Examples illustrating the use of naturally occurring or engineered KRED enzymes in biocatalytic processes to generate useful chemical compounds include asymmetric reduction of 4-chloroacetoacetate esters (Zhou, J. Am. Chem. Soc. 1983 105:5925-5926; Santaniello, J. Chem. Res. (S) 1984:132-133; U.S. Pat. Nos. 5,559,030; 5,700,670 and 5,891,685), reduction of dioxocarboxylic acids (e.g., U.S. Pat. No. 6,399,339), reduction of tert-butyl (S)-chloro-5-hydroxy-3-oxohexanoate (e.g., U.S. Pat. No. 6,645,746 and WO 01/40450), reduction pyrrolotriazine-based compounds (e.g., U.S. application No. 2006/0286646); reduction of substituted acetophenones (e.g., U.S. Pat. No. 6,800,477); and reduction of ketothiolanes (WO 2005/054491).

Several KRED gene and enzyme sequences have been reported, including: *Candida magnoliae* (Genbank Ace. No. JC7338; GI: 11360538); *Candida parapsilosis* (Genbank Ace. No. BAA24528.1; GI:2815409), Sporobolomyces *salmonicolor* (Genbank Ace. No. AF160799; GI:6539734); *Lactobacillus* kefir (Genbank Ace. No. AAP94029.1; GI: 33112056); *Lactobacillus brevis* (Genbank Ace. No. 1NXQ_A; GI: 30749782); *Exiguobacterium acetylicum* (Genbank Ace. No. BAD32703.1) and Thermoanaerobium brockii (Genbank Ace. No. P14941; GI: 1771790).

The KRED catalyzed reduction of compound (II) to compound (III) requires that an electron donor is present in the solution. Generally, a cofactor is used as the electron donor in the KRED reduction reaction. The cofactor operates in combination with the KRED and/or glucose dehydrogenase (abbreviated GDH) in the process. Suitable cofactors include, but are not limited to, NADP+(nicotinamide adenine dinucleotide phosphate), NADPH (the reduced form of NADP+), NAD+(nicotinamide adenine dinucleotide) and NADH (the reduced form of NAD+). Generally, the reduced form of the cofactor is added to the reaction mixture. Accordingly, the methods of the present disclosure are carried out wherein an electron donor is present selected from NADPH cofactor or NADH cofactor. In certain embodiments, the method can be carried out wherein the reaction conditions comprise an NADH or NADPH cofactor concentration of about 0.03-0.5 g/L, about 0.05-0.3 g/L, about 0.1-0.2 g/L, about 0.5 g/L, about 0.1 g/L, or about 0.2 g/L.

In some embodiments of the process, a cofactor recycling system is used to regenerate cofactor NADPH/NADH form NADP+/NAD+ produced in the reaction. A cofactor recycling system refers to a set of reactants that reduce the oxidized form of the cofactor (e.g., NADP+ to NADPH) thereby allowing the KRED catalysis to continue.

The cofactor recycling system may further comprise a secondary substrate and catalyst, for example, the substrate glucose, and the enzyme GDH, that catalyses the reduction of the oxidized form of the cofactor by the reductant.

Cofactor recycling systems to regenerate NADH or NADPH from NAD+ or NADP+, respectively, are known in the art and may be used in the methods described herein. Suitable exemplary cofactor recycling systems that may be employed include, but are not limited to, glucose and glucose dehydrogenase (GDH), formate and formate dehydrogenase (FDH), glucose-6-phosphate and glucose-6-phosphate dehydrogenase, a secondary alcohol and secondaralcohol dehydrogenase, phosphite and phosphite dehydrogenase, molecular hydrogen and hydrogenase, and the like.

Suitable secondary alcohols include lower secondary alcohols and aryl-alkyl carbinols. Examples of lower secondary alcohols include isopropanol, 2-butanol, 3-methyl-2-butanol, 2-pentanol, 3-pentanol, 3,3-dimethyl-2-butanol, and the like. In a particularly preferred embodiment the secondary alcohol is isopropyl alcohol (IPA). Suitable arylakyl carbinols include unsubstituted and substituted 1-arylethanols.

These systems may be used in combination with either NADP+/NADPH or NAD+/NADH as the cofactor.

Electrochemical regeneration using hydrogenase may also be used as a cofactor regeneration system. See, e.g., U.S. Pat. Nos. 5,538,867 and 6,495,023.

Chemical cofactor regeneration systems comprising a metal catalyst and a reducing agent (for example, molecular hydrogen or formate), may also be used in combination with either NADP+/NADPH or NAD+/NADH as the cofactor. See, e.g., PCT publication WO 2000/053731.

In some embodiments of the present disclosure, the cofactor recycling system can comprise glucose dehydrogenase (GDH), which is an NAD+ or NADP+-dependent enzyme that catalyses the conversion of D-glucose (dextrose) and NAD+ or NADP+ to gluconic acid and NADH or NADPH, respectively. GDH enzymes suitable for use in the practice of the processes described herein include both naturally occurring GDHs, as well as non-naturally occurring GDHs. Naturally occurring glucose dehydrogenase encoding genes have been reported in the literature, e.g., the *Bacillus subtilis* 61297 GDH gene, *B. cereus* ATCC 14579 and *B. megaterium*. Non-naturally occurring GDHs generated using, for example, mutagenesis, directed evolution, and the like and are provided in PCT publication WO 2005/018579, and US publication Nos. 2005/0095619 and 2005/0153417.

In some embodiments, the cofactor recycling system can comprise a formate dehydrogenase (FDH), which is an NAD+ or NADP+-dependent enzyme that catalyses the conversion of formate and NAD+ or NADP+ to carbon dioxide and NADH or NADPH, respectively.

As used herein, the term "formate" refers to formate anion (HCOO—), formic acid (HCOOH) and mixtures thereof.

FDHs suitable for use as cofactor regenerating systems in the KRED catalysed reaction described herein include naturally occurring and non-naturally occurring formate dehydrogenases. Suitable formate dehydrogenases are described in PCT publication WO 2005/018579.

Formate may be provided in the form of a salt, typically an alkali or ammonium salt (for example, $HCO_2Na$, $KHCO_2$, $NH_4HCO_2$, and the like), in the form of formic acid, typically aqueous formic acid, or mixtures thereof. A base or buffer may be used to provide the desired pH.

In some embodiments, the cofactor regenerating system can comprise the same KRED enzyme that catalyses the reduction of compound (II) to compound (III). In such an embodiment, the same KRED catalysing the reduction of compound (II) to compound (III) also catalyses the oxidation of a secondary alcohol (e.g., isopropanol to acetone oxidation) and thereby simultaneously reduces the NAD+ or NADP+ to NADH or NADPH. Accordingly, in some embodiments, the KRED catalysed conversion of compound (II) to compound (III) can be carried out in the presence of a secondary alcohol (e.g., IPA) and without any coenzyme (e.g., GDH) present in the solution for the recycling of the NADPH or NADH cofactor. In such embodiments, the suitable reaction conditions can comprise an IPA concentration is about 55-75% (v/v), an NADPH or NADH cofactor loading of about 0.03-0.5 g/L, and wherein no cofactor recycling enzyme is present other than the KRED itself.

In one embodiment, a KRED enzyme coupled with a cofactor recycling system and an NADPH cofactor is used to reduce (II) to obtain compound (III). Suitable reaction conditions for the KRED-catalyzed reduction of (II) to compound (III) are provided below and in the examples.

The enzymatic reduction step is carried out in a aqueous solvent.

The enzymatic reduction step is preferably carried out in a aqueous solvent and a co-solvent.

The co-solvent assists in enhancing solubility of compounds having poor water solubility, thereby increasing overall rate of the reaction. Suitable co-solvents include organic solvents, for example methanol, IPA, 1-octanol, ethyl acetate, methyl acetate, butyl acetate, heptane, octane, methyl t-butyl ether (MTBE), dimethyl sulfoxide (DMSO), tetrahydrofuran (THF), 2-methyltertahydrofuran (Me-THF), toluene and the like (including mixtures thereof), and ionic liquids, for example 1-ethyl-4-methylimidazolium tetra fluoroborate, 1-butyl-3-methylimidazolium tetrafluoroborate, 1-butyl-3-methylimidazolium hexafluorophosphate, and the like.

In some embodiments, aqueous solvents, including water and aqueous co-solvent systems, may be used.

The ratio of water to organic solvent in the co-solvent system is typically in the range of from about 90:10 to about 95:05 (v/v) water to organic solvent. Preferably the solvent does not exceed 5% of the total volume of the reaction solution.

The aqueous solvent (water or aqueous co-solvent system) may be pH-buffered or unbuffered. Generally, the reduction can be carried out at a pH of about 10 or below, usually in the range of from about 5 to about 10. In some embodiments, the reduction is carried out at a pH of about 9 or below, usually in the range of from about 5 to about 9. In some embodiments, the reduction is carried out at a pH of about 8 or below, often in the range of from about 5 to about 8, and usually in the range of from about 6 to about 8. The reduction may also be carried out at a pH of about 7.8 or below or 7.5 or below. In a preferred embodiment, the reduction is carried out at neutral pH, i.e. about 7.

During the course of the reduction reactions, the pH of the reaction mixture may change. The pH of the reaction mixture may be maintained at a desired pH or within a desired pH range by the addition of an acid or a base during the course of the reaction. Alternatively, the pH may be controlled by using an aqueous solvent that comprises a buffer.

Suitable buffers to maintain desired pH ranges are known in the art and include, for example, phosphate buffer, triethanolamine buffer, and the like. Combinations of buffering and acid or base addition may also be used.

According to a preferred embodiment, the process of the present invention, can be carried out in presence of phosphate buffer at pH 7.

Other buffer solution that could be used to carry out the above mentioned reaction, such as is, for instance, Tris (hydroxymethyl)aminomethane hydrochloride buffer.

Suitable bases for neutralization are organic bases, for example amines, alkoxides and the like, and inorganic bases; for example, hydroxide salts (e.g., NaOH), bicarbonate salts (e.g. NaHCO$_3$), carbonate salts (e.g. K$_2$CO$_3$), basic phosphate salts (e.g. K$_2$HPO$_4$, Na$_3$PO$_4$), and the like.

Suitable acids to add during the course of the reaction to maintain the pH include organic acids, for example carboxylic acids, sulfonic acids, phosphoric acids, and the like, mineral acids, for example hydrohalic acids (such as hydrochloric acid), sulphuric acid, phosphoric acid, and the like, acidic salts, for example dihydrogen phosphate salts (e.g., KH$_2$PO$_4$), bisulphate salts (e.g., NaHSO$_4$) and the like. Some embodiments utilize formic acid, whereby both the formate concentration and the pH of the solution are maintained.

The reduction step is typically carried out at a temperature in the range of from about 0° C. to about 75° C. Preferably, the reduction step is carried out at a temperature in the range of from about 10° C. to about 55° C. In still other embodiments, it is carried out at a temperature in the range of from about 20° C. to about 45° C. In a particularly preferred embodiment the reaction is carried out under ambient conditions or room temperature.

The step B) of the process according to the invention can be comprising a step b-1) of conversion of $R^1$ and/or $R^2$ from acetyl to hydrogen.

In an alternative embodiments, the step B) of the process according to the invention can be comprising the step b-1) of conversion of $R^1$ and $R^2$ from methyl or benzyl or a $C_1$-$C_4$ alkyl groups joined to form a cycle in to hydrogen.

The step B) of the process according to the invention can be comprising the step b-1a) of conversion of $R^1$ from acetyl, methyl, benzyl, a $C_1$-$C_4$ alkyl groups joined to form a cycle to hydrogen;
i.e. to obtain the compound of formula (IV):

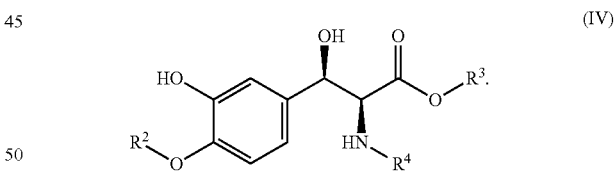

(IV)

The step B) of the process according to the invention can be comprising the step b-1b) of conversion of $R^2$ from acetyl, methyl, benzyl, a $C_1$-$C_4$ alkyl groups joined to form a cycle to hydrogen;
i.e. to obtain the compound of formula (V):

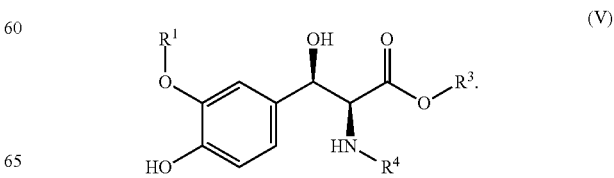

(V)

The step B) of the process according to the invention can be comprising the step b-1) of simultaneous conversion of $R^1$ and $R^2$ from acetyl, methyl, benzyl, a $C_1$-$C_4$ alkyl groups joined to form a cycle to hydrogen;

i.e. to obtain the compound of formula (VI):

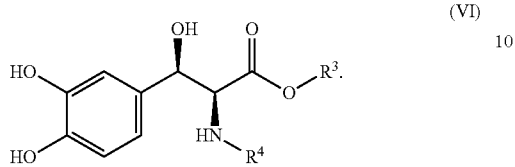

(VI)

The step b-1) of the process according to the invention can be a step of hydrolysis of the esteric group when $R^1$ and $R^2$ are acetyl.

The step b-1) of the process according to the invention can be a step of conversion of $R^1$ and $R^2$ to hydrogen, depending on the nature of the $R^1$ and $R^2$, can be carried out differently, using the common general knowledge of the skilled person, evidence of the which can be found in the book of Theodora W Greene with title "Protective Groups in Organic Synthesis" (3rt edition 1999) or in the book of Anthony J. Pearson with title "Handbook of Reagents for Organic Synthesis—Activating Agents and Protecting Groups".

The step B) of the process according to the invention can be comprising a step b-2) of conversion of $R^3$ from a $C_1$-$C_4$ linear or branched alkyl group to hydrogen;

i.e. to obtain the compound of formula (VII):

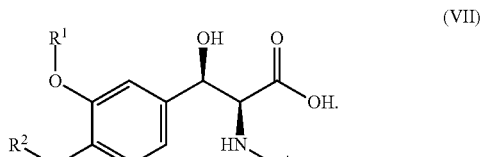

(VII)

The step b-2) of the process according to the invention can be a step of conversion of $R^3$ to hydrogen (i.e. hydrolysis of the esteric group), depending on the nature of the $R^3$, can be carried out differently, using the common general knowledge of the skilled person, evidence of the which can be found in the book of Theodora W Greene with title "Protective Groups in Organic Synthesis" or in the book of Anthony J. Pearson with title "Handbook of Reagents for Organic Synthesis—Activating Agents and Protecting Groups".

Suitable process for removal (i.e. conversion of $R^3$ to hydrogen) $R^3$, when is a $C_1$-$C_4$ linear or branched alkyl group, is an hydrolysis. This process requires a treatment of the compound of formula (III) with a solution of base (e.g. NaOH, KOH, LiOH) in water or an alcoholic solvent or a mixture thereof.

The step B) of the process according to the invention can be comprising a step b-3) of conversion of $R^4$ from amine protecting group to hydrogen;

i.e. to obtain the compound of formula (VIII):

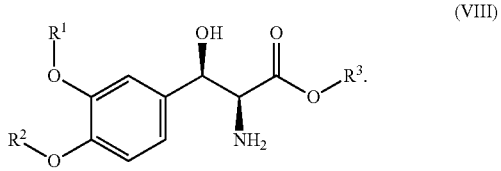

(VIII)

The step b-3) of the process according to the invention can be a step of cleavage of amine protecting group.

The step b-3) of the process according to the invention can be comprising the step of conversion of $R^4$ to hydrogen (i.e. cleavage of amine protecting group), depending on the nature of the $R^4$, can be carried out differently, using the common general knowledge of the skilled person, evidence of the which can be found in the book of Theodora W Greene with title "Protective Groups in Organic Synthesis" ($3^{rd}$ ed. 1999) or in the book of Anthony J. Pearson with title "Handbook of Reagents for Organic Synthesis—Activating Agents and Protecting Groups" (1999).

According to a preferred embodiment, the step b-1), b-2) and b-3) can be made in any combination of order.

According to a preferred embodiment, the step B) of the process of the present invention, can be comprising the step of simultaneous hydrolysis of the esteric group and cleavage of amine protecting group.

According to a preferred embodiment, the step B) of the process of the present invention, can be comprising the step of simultaneous conversion of $R^3$ from a $C_1$-$C_4$ linear or branched alkyl group to hydrogen and conversion of $R^4$ from amine protecting group to hydrogen;

i.e. to obtain the compound of formula (IX):

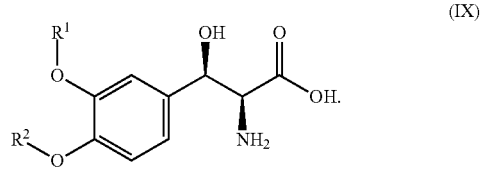

(IX)

According to a preferred embodiment, the step B) of the process of the present invention, is characterized in the simultaneous:

conversion of $R^1$ and $R^2$ from acetyl, methyl, benzyl, a $C_1$-$C_4$ alkyl groups joined to form a cycle to hydrogen;

conversion of $R^3$ from a $C_1$-$C_4$ linear or branched alkyl group to hydrogen;

i.e. to obtain the compound of formula (X):

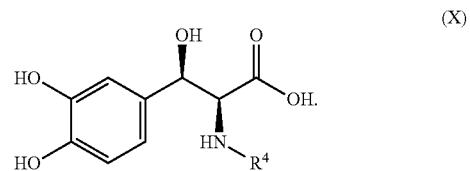

(X)

According to a preferred embodiment, the step B) of the process of the present invention, is characterized in the simultaneous:
conversion of $R^1$ and $R^2$ from acetyl, methyl, benzyl, a $C_1$-$C_4$ alkyl groups joined to form a cycle to hydrogen;
conversion of $R^4$ from amine protecting group to hydrogen;
i.e. to obtain the compound of formula (XI):

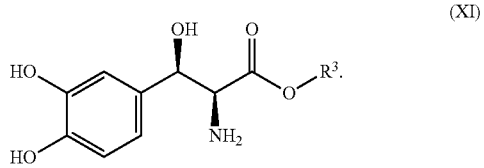

According to a preferred embodiment, the step B) of the process of the present invention, is characterized in the simultaneous:
conversion of $R^1$ and $R^2$ from acetyl to hydrogen;
conversion of $R^3$ from a $C_1$-$C_4$ linear or branched alkyl group to hydrogen;
i.e. to obtain the compound of formula (X).

According to a preferred embodiment, the step B) of the process of the present invention, is characterized in the simultaneous:
conversion of $R^1$ and $R^2$ from acetyl to hydrogen;
conversion of $R^4$ from amine protecting group to hydrogen; i.e. to obtain the compound of formula (XI).

According to a preferred embodiment, the step B) of the process of the present invention, is characterized in the simultaneous:
conversion of $R^1$ and $R^2$ from acetyl to hydrogen;
conversion of $R^3$ from a $C_1$-$C_4$ linear or branched alkyl group to hydrogen;
conversion of $R^4$ from amine protecting group to hydrogen;
i.e. to obtain the compound of formula (I):

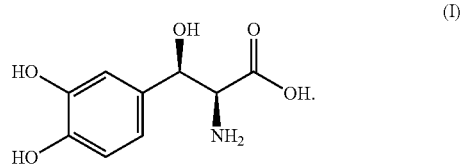 [SMILES: N[C@H](C(=O)O)[C@H](O)c1ccc(O)c(O)c1]

The step B) of the process according to the invention can be comprising a step or steps of purification or resolution by crystallisation.

According to a preferred embodiment, the step B) can be comprising a step b-4) of purification or resolution of the compound of formula (III) or (IV) or (V) or (VI) or (VII) or (VIII) or (IX) or (X) or (XI); its allows an efficient purging of the undesired isomer, to obtain an efficient enrichment in terms of enantiomeric excess.

The process of the present invention, at the end of the step B), thus provides Droxidopa having high optical purity, i.e. Droxidopa having typically an optical purity higher than 99.0% (e.e.), i.e. higher than 99.5% expressed as HPLC A/A %.

Preferably, the process of the present invention provides Droxidopa having high optical purity, i.e. Droxidopa having typically an optical purity higher than 99.4% (e.e.), i.e. higher than 99.7% HPLC A/A %.

The enantiomeric excess or "e.e." or "ee" for short is defined as the absolute difference between the mole fractions of two enantiomers and it is often presented as percent enantiomeric excess, % ee, which is obtained by the following calculation: % ee=R−S/R+S×100%, wherein the amount of the single enantiomers can be often measured by chiral chromatography.

Obviously and optionally, the process of the present invention can be re-applied on the already optically purified Droxidopa so that Droxidopa having optical purity of 100% can be prepared.

The ratio between the optical isomers threo and erythro from 50:50 to 99:1, is intended as ratio weight by weight which, however, corresponds to the amount determined by HPLC A/A %.

According to a preferred embodiment of the process of the present invention, compound of formula (I) has an diastereoisomeric ratio between threo and erythro (threo/erythro) comprised from 50/50 to 90/10, more preferred from 50/50 to 70/30.

According to a more preferred embodiment of the process of the present invention, compound of formula (I) has an diastereoisomeric ratio 70/30 between threo and erythro (threo/erythro).

According to a preferred embodiment of the present invention, in the step b-4), the ratio between the optical isomers of the compound (III) or (IV) or (V) or (VI) or (VII) or (VIII) or (IX) or (X) or (XI), is from 75:25 to 85:15 since this ratio of isomers is that typically achieved by an enzymatic reduction of the process of the present invention.

Examples illustrating the purification or resolution by crystallization processes, using the common general knowledge of the skilled person, evidence of the which can be found Japanese Patent Application 49,252/75, 36,233/79, 29,551/81 and 32,540/76; European Patent No. 084928; No. 128684; U.S. Pat. No. 3,920,728.

According to a preferred embodiment of the process of the present invention, the reaction of compound of formula (II) to give compound of formula (I) occurs with a conversion comprised in the range from 20% to at least 95%.

In particular, when the reaction is carried out with an KRED KRED-130, conversion is at least 95%.

In particular, compound of formula (I) has diastereoisomeric ratio 70/30 between threo and erythro (threo/erythro), when the reaction compound of formula (II) is carried out with an KRED KRED-130.

According to a preferred embodiment of the process of the present invention, compound of formula (I) has diastereoisomeric ratio at least 75/30 (threo/erythro), and the employed KRED KRED-130.

According to a preferred embodiment of the process of the present invention, the reaction of compound of formula (II) to give compound of formula (III) occurs with a conversion comprised in the range from 20% to at least 95%.

In particular, when the reaction is carried out with an KRED KRED-130, conversion is at least 95%.

According to a preferred embodiment of the process of the present invention, compound of formula (III) has an diastereoisomeric ratio between threo and erythro (threo/erythro) comprised from 50/50 to 90/10, more preferred from 50/50 to 70/30.

According to a more preferred embodiment of the process of the present invention, compound of formula (III) has an diastereoisomeric ratio 70/30 between threo and erythro (threo/erythro).

In particular, compound of formula (III) has diastereoisomeric ratio 70/30 between threo and erythro (threo/erythro), when the reaction compound of formula (II) is carried out with an KRED KRED-130.

According to a preferred embodiment of the process of the present invention, compound of formula (III) has diastereoisomeric ratio at least 75/30 (threo/erythro), and the employed KRED KRED-130.

The diastereoisomeric ratio is defined as the absolute ratio between the mole fractions of threo isomer and the mole fraction of erythro isomer, which is obtained by the following calculation: ratio=|Threo|/|Erythro|, wherein the amount of the single enantiomers can be often measured by chiral chromatography.

The compound of formula (III):

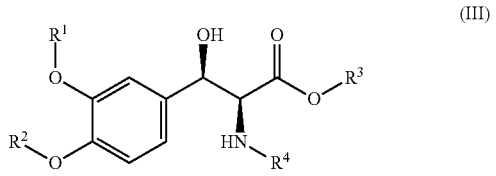

wherein $R^1$, $R^2$ are independently hydrogen or acetyl, $R^3$ is hydrogen, a $C_1$-$C_4$ linear or branched alkyl group and $R^4$ is hydrogen or an amine protecting group;
can be thus prepared by a process comprising a step of enzymatic reduction of a compound of formula (II):

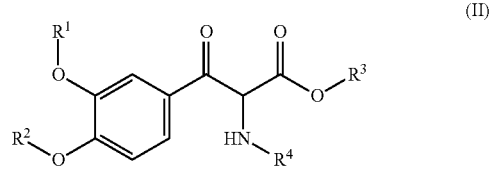

wherein $R^1$, $R^2$, $R^3$, $R^4$ have the same meaning of above; by means of a ketoreductase enzyme.

The compound of formula (II):

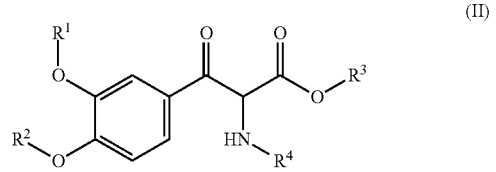

wherein $R^1$, $R^2$ are independently hydrogen or acetyl, $R^3$ is hydrogen, a $C_1$-$C_4$ linear or branched alkyl group and $R^4$ is hydrogen or an amine protecting group;
can be used for the preparations of compound of formula (III):

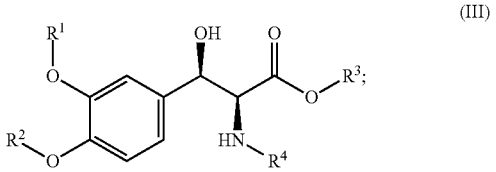

wherein $R^1$, $R^2$, $R^3$, $R^4$ have the same meaning of above; or for the preparation of Droxidopa of formula (I) or salt thereof:

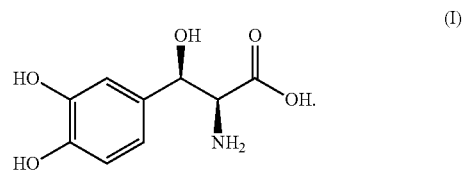 [SMILES: N[C@H](C(=O)O)[C@H](O)c1ccc(O)c(O)c1]

A ketoreductase can be thus used to carry out the enzymatic reduction of compound of formula (II):

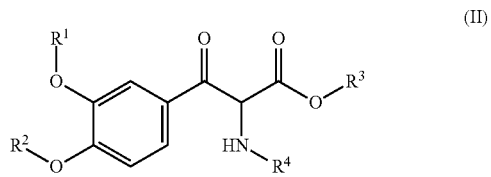

wherein $R^1$, $R^2$ are independently hydrogen or acetyl, $R^3$ is hydrogen, a $C_1$-$C_4$ linear or branched alkyl group and $R^4$ is hydrogen or an amine protecting group, to provide a compound of formula (III):

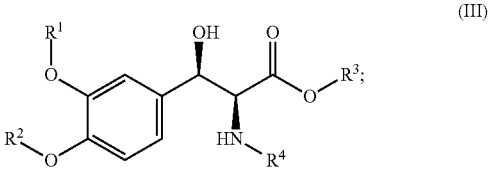

wherein $R^1$, $R^2$, $R^3$, $R^4$ have the same meaning of above; or to provide Droxidopa of formula (I) or salt thereof:

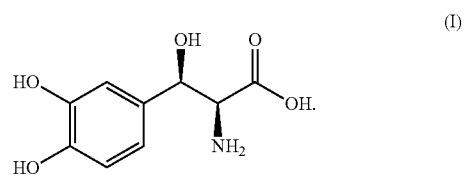 [SMILES: N[C@H](C(=O)O)[C@H](O)c1ccc(O)c(O)c1]

Thus, according to a preferred embodiment, the ketoreductase used for the carried out the enzymatic reduction of the compound of formula (II), is KRED-130.

The process of the present invention thus also provides new intermediates, i.e. the compound of formula (II):

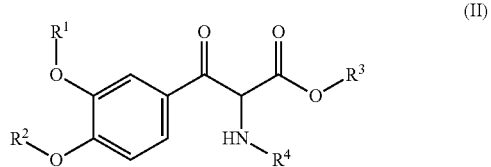

wherein $R^1$, $R^2$ are independently hydrogen or acetyl, $R^3$ is hydrogen, a $C_1$-$C_4$ linear or branched alkyl group and $R^4$ is hydrogen or an amine protecting group.

The process of the present invention thus also provides new intermediates, i.e. the compound of formula (III):

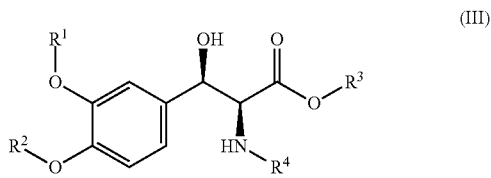

(III)

wherein $R^1$, $R^2$ are independently hydrogen or acetyl, $R^3$ is hydrogen, a $C_1$-$C_4$ linear or branched alkyl group and $R^4$ is hydrogen or an amine protecting group;
with the exception of the compounds wherein:
- $R^1$, $R^2$ and $R^4$ are hydrogen, $R^3$ is methyl;
- $R^1$, $R^2$ and $R^4$ are hydrogen, $R^3$ is ethyl;
- $R^1$ and $R^2$ are hydrogen, acetyl, $R^3$ is ethyl and $R^4$ is acetyl;
- $R^1$, $R^2$ and $R^4$ are acetyl, $R^3$ is ethyl.

Further, the enzymatic reduction process is environmentally advantageous as compared to the prior art process wherein organometallic chiral catalyst are used in the prior art. The use of an enzyme as the reducing agent is cheaper compared to the use of a organometallic chiral catalyst. In addition, resolution using chiral amine according to known methods leads to about 50% loss of undesired isomer and hence it is not industrially suitable.

EXPERIMENTAL SECTION

The ketoreductase enzyme are largely commercially available, for example, for supplied by Codexis (USA), for example the Codexis® KRED screening kit.

The starting material compound of formula (II) having the following formula or:

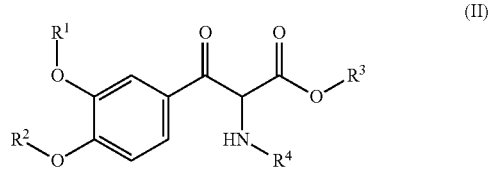

(II)

wherein $R^1$, $R^2$ are independently hydrogen or acetyl, $R^3$ is hydrogen or a $C_1$-$C_4$ linear or branched alkyl group and $R^4$ is hydrogen or an amine protecting group; are prepared according to the know prior art method of synthesis.

A few methods for the preparation of compound of formula (II) have been described, for example, Kazuishi Makino at all in Journal of the American Chemical Society (2005), 127, (16), 5784-5785; Brinton Seashore-Ludlow at all in Organic Letters (2010), 12, (22), 5274-5277; Zheng Long-Sheng at all in Chemical Communications, 54(3), 283-286; 2018; Guan, Yu-Qing at all in Chemical Communications, 53(58), 8136-8139; 2017; Seashore-Ludlow, Brinton at all in Chemistry A European Journal, 18(23), 7219-7223, 2012.

Volumes means volume of solvent per unit of product, thus, for example, 1 volume is 1 Liter per 1 Kilo, or 1 mL for 1 gram, or 1 microliter per 1 milligram. Thus, 10 volumes means for example 10 liters per 1 Kilogram of substance.

Example 1: Use of Codexis® KRED kit in the enzymatic reduction of compound of formula (II) wherein $R^1$ and $R^2$ is acetyl, $R^3$ is ethyl, $R^4$ is Boc.

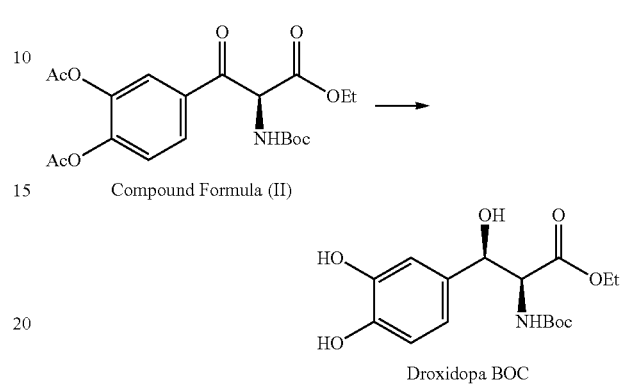

The reaction were performed in 1 ml in a vial and shaken overnight at room temperature for the isopropanol dependent enzymes, the condition of reaction were: 115.2 mM sodium phosphate buffer, 1.53 mM magnesium sulphate, 1 mM NADP+, 10% v/v isopropanol, 10 mg/ml of compound of formula (II) wherein $R^1$ and $R^2$ is acetyl, $R^3$ is ethyl, $R^4$ is Boc., 10 mg/ml of enzyme, pH 7.

For the glucose dependent enzymes the condition of reaction were: 128 mM sodium phosphate 1.7 mM magnesium sulphate, 1.1 mM NADP+1.1 mM NAD+, 80 mM D-glucose, 4.3 U/ml glucose dehydrogenase, 10 mg/ml of compound of formula (II) wherein $R^1$ and $R^2$ is acetyl, $R^3$ is ethyl, $R^4$ is Boc., pH 7.

The reaction was analysed in HPLC-MS to confirm desiderated product mass. Also the chiral purity was evaluated by HPLC and was observed between the threo and erythro form.

Example 2: Synthesis of Droxidopa BOC of formula (I) by enzymatic reduction of the compound of formula (II) wherein R1 and R2 is acetyl, R3 is ethyl, R4 is Boc.

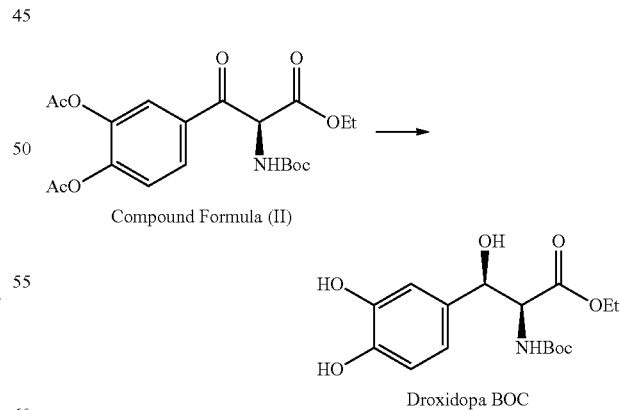

To 1 g of compound of formula (II) (wherein $R^1$ and $R^2$ is acetyl, $R^3$ is ethyl, $R^4$ is Boc) was added 20 mg of $MgSO_4$, 50 mg of CDX-901 (cofactor regeneration enzyme, glucose dehydrogenase), 200 mg of KRED-130, 50 mg of NADP+, 1 g of Glucose in 50 ml of 100 mM phosphate buffer at pH 7. The reaction was performed at 25° C. and it was maintained at pH 7 by addition of NaOH 0.5 M by automatic titration. After 64 h of reaction analysis give about 80 A % of Droxydopa BOC. The reaction was quenched with 100 ml of EtOAc and 1 g of dicalite and filtered to removed enzyme and organic layer was separated. Aqueous layer was washed twice with 100 ml of EtOAc. Join organic layer was distilled to residue obtaining 0.7 g of crude of the Droxydopa BOC. Product analysed by HPLC-MS analysis.

Example 3: Synthesis of Droxidopa BOC of formula (I) by enzymatic reduction of the compound of formula (II) wherein R1 and R2 is acetyl, R3 is ethyl, R4 is BOC.

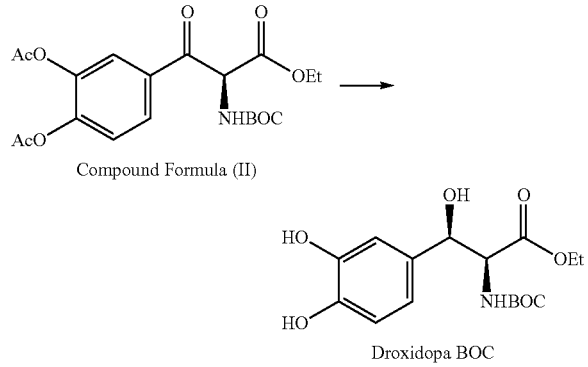

Compound Formula (II)

Droxidopa BOC

To 3.0 g of compound of formula (II) (wherein $R^1$ and $R^2$ is acetyl, $R^3$ is ethyl, $R^4$ is BOC) was added to a solution of 60 mg of $MgSO_4$, 150 mg of CDX-901 (cofactor regeneration enzyme, glucose dehydrogenase), 600 mg of KRED-130, 150 mg of NADP+, 3 g of Glucose in 150 ml of 100 mM phosphate buffer at pH 7. The reaction mixture was stirred at 25° C. and it was maintained at pH 7 by addition of NaOH 0.5 M by automatic titration. After 15 and 24 h of reaction 150 mg of NADP+ and 150 mg of CDX-901 were added. The reaction conversion was monitored by HPLC, and after 120 h the reaction was quenched with 100 ml of EtOAc and 1 g of dicalite, then the suspension was filtered to remove the enzyme and organic layer was separated. Aqueous layer was washed twice with 50 ml of EtOAc. The jointed organic layer was dried with $Na_2SO_4$ and distilled to residue obtaining 3.0 g of crude of Droxidopa BOC that spontaneously crystalized. Analysis of isolate crystal Droxidopa BOC was about 60 A %.

Example 4: Synthesis of Droxidopa Ethyl Estere of formula (I) by by chemical cleavage of Boc N-protection group.

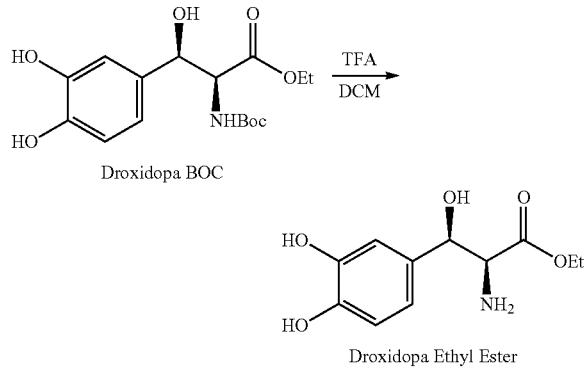

Droxidopa BOC

Droxidopa Ethyl Ester

To 70 mg of Droxidopa BOC obtained in the example 3 was dissolved in 1 ml of dichloromethane. At 25° C. was added 1 ml of TFA and the conversion was monitored by HPLC. After complete cleavage of BOC the product Droxidopa ethyl ester was isolated by concentration to residue with a flow of nitrogen.

Example 5: Synthesis of Droxidopa of formula (I) by chemical hydrolysis of R3, wherein R3 is ethyl.

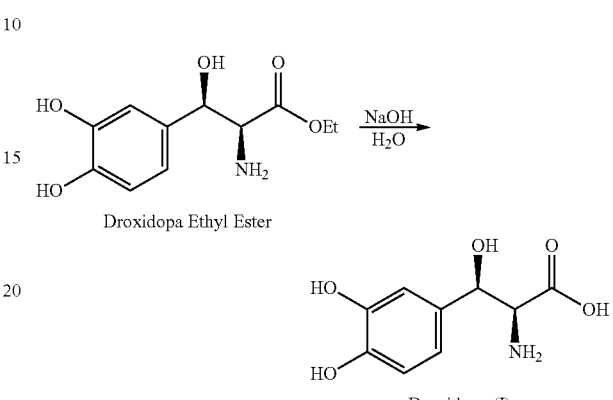

Droxidopa Ethyl Ester

Droxidopa (I)

To 25 mg of isolated Droxydopa ethyl ester obtained in the example 4 was added to 1 ml of NaOH 3M. The reaction was mixed for 2 h at room temperature and monitored by HPLC. After complete hydrolysis the reaction was neutralized with HCl 10% solution and crude Droxidopa was isolated by concentration the solution to residue with a flow of nitrogen. Isolated Droxidopa was analysed for diastereoisomeric purity by HPLC, where a ratio of 70:30 A % was observed between the threo Droxydopa and erythro Droxydopa form.

Example 6: Synthesis of Droxidopa Ethyl Estere of formula (I) by chemical cleavage of Boc N-protection group.

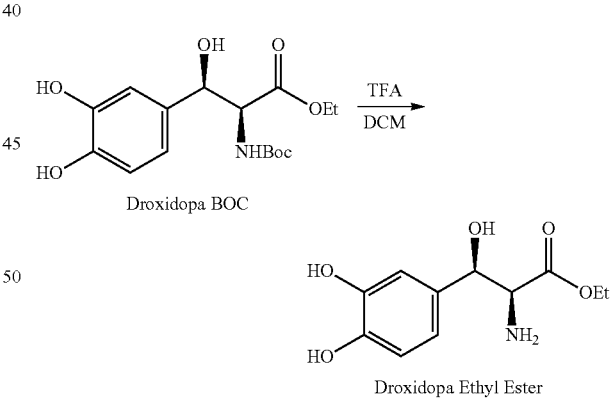

Droxidopa BOC

Droxidopa Ethyl Ester

To 1 g of crude Droxidopa BOC obtained in the example 3 was dissolved in 10 ml of dichloromethane. At 25° C. was added 1.5 ml of TFA and conversion monitored by HPLC. After complete cleavage of BOC, the pH was neutralized with addition of saturated solution of $NaHCO_3$. The product was isolated by concentration to residue obtaining about 1.3 g of crude Droxidopa ethyl ester. Isolated product was analysed in HPLC-MS to confirm mass (Mw 241). Also the diastereoisomeric purity was evaluated by HPLC, where a ratio of 72:28 A % was observed between the threo and erythro form.

Example 7: Synthesis of Droxidopa of formula (I) by chemical hydrolysis of R3, wherein R3 is ethyl.

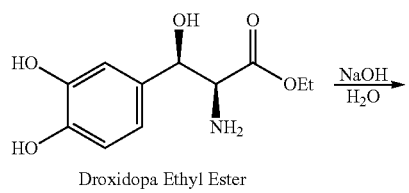

Droxidopa Ethyl Ester

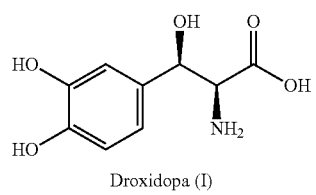

Droxidopa (I)

To 100 mg of isolated Droxydopa ethyl ester from example 6 was added to 1 ml of water. Then 100 μl of NaOH 10M was added and mix for 30 min. The reaction was monitored by HPLC. After complete hydrolysis, the reaction was neutralized with HCl 10% solution and crude Droxidopa isolated by concentration to residue with a flow of nitrogen. The isolated product, about 100 mg, was analysed for evaluate diastereoisomeric purity by HPLC. A ratio of 70:30 A % was observed between the threo Droxydopa and erythro Droxydopa form.

Example 8: Synthesis of Droxidopa BOC of formula (I) by enzymatic reduction of the compound of formula (II) wherein R1 and R2 is acetyl, R3 is ethyl, R4 is BOC.

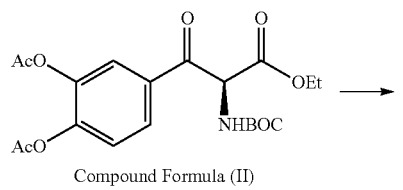

Compound Formula (II)

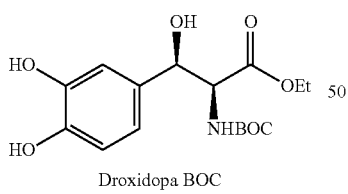

Droxidopa BOC

In 75 ml of 50 mM phosphate buffer at pH 7 was added 20 mg of $MgSO_4$, mg of CDX-901 (cofactor regeneration enzyme, glucose dehydrogenase), 200 mg of KRED-130, 75 mg of NADP+, 1.3 g of Glucose. The suspension was mix at 30° C. and pH correct to 7 with NaOH 0.5 M. Subsequently a solution composed by 1.5 g of compound of formula (II) (wherein $R^1$ and $R^2$ is acetyl, $R^3$ is ethyl, $R^4$ is BOC) dissolved in 3.25 ml of DMSO was added in 10 min to the suspension. The reaction was performed at 30° C. and it was maintained at pH 7 by addition of NaOH 0.5 M by automatic titration. After 9 h and 17 h of reaction were added 75 mg of NADP+ and 25 mg of CDX-901. The reaction conversion was monitored by HPLC, and after 22 h the reaction was filtered to removed undissolved material. To the mother liquor was added 50 ml of EtOAc and 1.5 g of dicalite, mixed for 30 min, then it was filtered and filtrated washed with 50 ml of EtOAc. To the obtained solution was added 20 ml of NaCl and organic layer separated. Aqueous layer was extracted again with 20 ml of EtAc and the joined organic layer wash with 30 ml of water. The organic layer was distilled to residue and stripped twice with 30 ml of DCM. Finally 0.9 g of Droxidopa BOC was obtained and analysed.

Example 9: Synthesis of Droxidopa Ethyl Estere of formula (I) by chemical cleavage of Boc N-protection group.

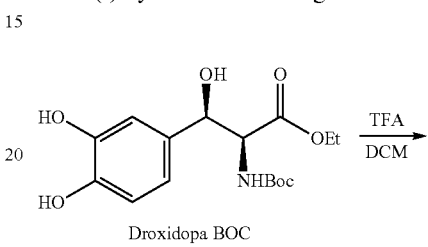

Droxidopa BOC

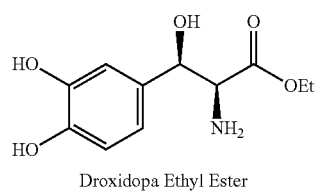

Droxidopa Ethyl Ester

To 0.9 g of Droxidopa BOC obtained in the example 8, was dissolved in 10 ml of dichloromethane. Then to the obtained solution at 25° C. was added 1.5 ml of TFA in 10 min. The obtained reaction mixture was stirred at 25° C. foe 1 h. Conversion was monitored by HPLC. After complete cleavage of BOC, the pH was neutralized with addition of saturated solution of $NaHCO_3$. The product was isolated by evaporation to residue obtaining about 0.9 g of crude Droxidopa ethyl ester. Isolated product was analysed in HPLC-MS to confirm mass (Mw 241). Also the diastereoisomeric purity was evaluated by HPLC, where a ratio of 72:28 A % was observed between the putative threo and erythro form.

Example 10: Synthesis of Droxidopa of formula (I) by chemical hydrolysis of R3, wherein R3 is ethyl.

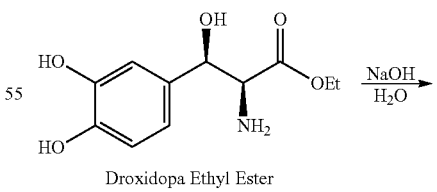

Droxidopa Ethyl Ester

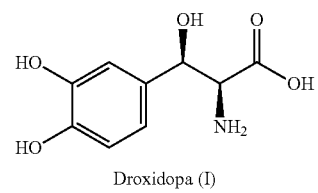

Droxidopa (I)

To 0.5 mg of isolated Droxydopa ethyl ester obtained in the example 9 was added to 6 ml NaOH 3 M. The reaction mixture was stirred for 1 h at 25° C. and conversion monitored by HPLC. After complete hydrolysis, the reaction was neutralized with HCl 10% solution and crude Droxidopa was isolated by concentration the solution to residue with flow of nitrogen. The isolated product, about 0.5 g was analysed for evaluate diastereisomeric purity by HPLC, where a ratio of 72:28 A % was observed between the threo Droxydopa and erythro Droxydopa form.

Example 11: Analytical method to analyse the reaction product.

Determination of purity, diastereoisomeric purity and assay by HPLC:

Chromatographic Conditions:

Column: Luna C18(2) 100 Å, 150×4.6 mm, 3.0 μm

Mobile phase A: Dissolve 1.0 g of sodium 1-heptanesulfonate and 1.36 g of potassium dihydrogen phosphate in 1000 mL of water and adjust the pH to 2.0 with phosphoric acid. To 930 mL of this solution add 70 mL of acetonitrile.

Detector: UV at 220 nm

Flow Rate: 1.0 mL/min.

Column Temperature: 25° C.

Injection volume: 50 μL

Run time: 35 minutes

Diluent: MilliQ water.

The invention claimed is:

1. A process for the preparation of Droxidopa of formula (I) or a salt thereof:

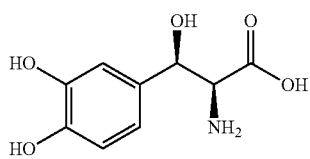

(I)

comprising the following steps:

A) enzymatically reducing a compound of formula (II):

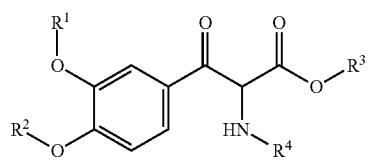

(II)

wherein $R^1$ and $R^2$ are independently hydrogen or acetyl, $R^3$ is hydrogen or a C1-C4 linear or branched alkyl group and $R^4$ is hydrogen or an amine protecting group;

with a ketoreductase enzyme to give the compound of formula (III):

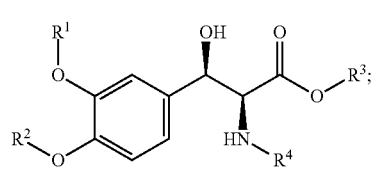

(III)

and if at least one of $R^1$, $R^2$, $R^3$ and $R^4$ is not H,

B) converting the compound of formula (III) to Droxidopa of formula (I).

2. The process according to claim 1, wherein the ketoreductase enzyme is KRED-130.

3. The process according to claim 1, wherein in the compounds of formula (II) and formula (III) $R^3$ is ethyl or methyl.

4. The process according to claim 1, wherein in the compounds of formula (II) and formula (III) $R^4$ is tert-butyloxycarbonyl, benzyloxycarbonyl, methyloxycarbonyl or ethyloxycarbonyl.

5. The process according to claim 1, wherein in the compounds of formula (II) and formula (III) $R^3$ is ethyl and $R^4$ is tert-butyloxycarbonyl.

6. The process according to claim 1, wherein step B) comprises a step of converting $R^1$ and/or $R^2$ from acetyl to hydrogen.

7. The process according to claim 1, wherein step B) comprises a step of converting $R^3$ from a C1-C4 linear or branched alkyl group to hydrogen.

8. The process according to claim 1, wherein step B) comprises a step of converting $R^4$ from an amine protecting group to hydrogen.

9. A process for the preparation of the compound of formula (III):

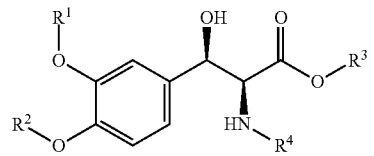

wherein $R^1$ and $R^2$ are independently hydrogen or acetyl, $R^3$ is hydrogen or a $C_1$-$C_4$ linear or branched alkyl group and $R^4$ is hydrogen or an amine protecting group;

comprising enzymatically reducing a compound of formula (II):

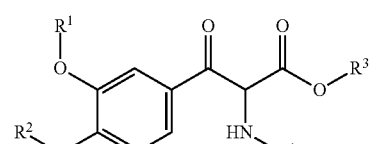

(II)

wherein $-R^1$, and $R^2$ are independently hydrogen or acetyl, $R^3$ is hydrogen or a $C_1$-$C_4$ linear or branched alkyl group and $R^4$ is hydrogen or an amine protecting group;

with a ketoreductase enzyme.

* * * * *